United States Patent [19]
Harms et al.

[11] Patent Number: 5,364,385
[45] Date of Patent: Nov. 15, 1994

[54] STORAGE BAG FOR BLOOD AND BLOOD COMPONENTS

[75] Inventors: Frank H. Harms, Marietta, Ga.; John R. Beard, Memphis, Tenn.; Alexander Duncan, Dunwoody, Ga.

[73] Assignee: LifeSource Advanced Blood Bank Systems, Inc., Atlanta, Ga.

[21] Appl. No.: 521,248

[22] Filed: May 9, 1990

[51] Int. Cl.⁵ .................................... A61M 1/00
[52] U.S. Cl. ............................ 604/410; 604/403; 604/408
[58] Field of Search .................. 604/408–411, 604/403, 4–6

[56] References Cited

U.S. PATENT DOCUMENTS

| | | |
|---|---|---|
| 3,915,212 | 10/1975 | Bujan et al. |
| 4,309,592 | 1/1982 | Le Boeuf |
| 4,365,629 | 12/1982 | Pert et al. |
| 4,559,053 | 12/1985 | Porges |
| 4,608,043 | 8/1986 | Larkin ........................ 604/410 X |
| 4,675,019 | 6/1987 | Bellhouse et al. |
| 4,707,587 | 11/1987 | Greenblatt |
| 4,731,072 | 3/1988 | Aid ............................. 604/408 |
| 4,743,236 | 5/1988 | Manschot |
| 4,790,815 | 12/1988 | Balteau et al. |
| 4,955,877 | 9/1990 | Kurtz et al. ................ 604/408 |
| 4,994,021 | 2/1991 | Smith et al. ............... 604/409 X |
| 4,994,039 | 2/1991 | Mattson .................... 604/408 |
| 5,017,338 | 5/1991 | Surgenor .................. 604/408 X |

FOREIGN PATENT DOCUMENTS

283126A 12/1988 European Pat. Off.

OTHER PUBLICATIONS

Inventory Control Systems Advertising Brochure, Cryogenic Equipment Corporation (1981).

Primary Examiner—Sam Rimell
Attorney, Agent, or Firm—Warren Franz

[57] ABSTRACT

A bag is disclosed for the collection, freezing, storage, and rapid thawing of fluids, and particularly blood and blood components. Front and back sheets of fluid impervious material are bonded to one another along edge portions thereof to form a bag defining a reservoir. The front and back sheets are further bonded together at a plurality of locations intermediate the edge portions to constrain the distance by which the front and back sheets can separate. The intermediate fastening locations are disposed to permit uniform filling of the reservoir. A port is provided for introducing and discharging fluid into and out of the reservoir. When a fluid is introduced into the reservoir, the front and back sheets are constrained from separating in response to a pressure exerted by the fluid by the intermediate fastenings between the front and back sheets to constrain the thickness of the bag. The distance between the centermost points in the interior of the bag and the corresponding closest points on the exterior of the bag is thereby minimized, increasing the rate at which heat is transferred into or out of the bag contents. Heat transfer is thus greatly improved, markedly reducing the time required to freeze or thaw the bag contents.

17 Claims, 3 Drawing Sheets

STORAGE BAG FOR BLOOD AND BLOOD COMPONENTS

TECHNICAL FIELD

The present application relates generally to an apparatus for storing a liquid or suspension for freezing and subsequent thawing, and relates more specifically to an apparatus for the rapid and hygienic freezing, storage, and subsequent rapid and hygienic thawing of fresh-frozen blood and blood components.

BACKGROUND OF THE INVENTION

A readily available supply of plasma and whole blood is an essential requirement of any medical trauma treatment facility. Since plasma can be stored at room temperature for a matter of only a few hours before spoilage occurs, it is conventional practice to freeze blood components. Whole blood can be stored only forty days before spoilage occurs and hence must be frozen if storage for longer periods is anticipated. Typically, plasma and whole blood are frozen within six hours after collection, in polyvinyl chloride bags holding about 300 milliliters. The fresh-frozen plasma is subsequently stored at temperatures of around −30° C., and fresh-frozen whole blood is stored at temperatures of around −80° C. When properly frozen, blood and blood components may be stored for up to ten years.

While the procedure of fresh-freezing blood and blood components has essentially solved the problems of storage, the process of thawing the product for use presents certain difficulties. When whole blood or platelets are being thawed, possible damage to cells during thawing is a major concern. While post-thaw viability of cellular structures is not of concern in thawing plasma, the viability of coagulation proteins is of primary importance. The most widely accepted method of thawing fresh-frozen blood and blood components comprises immersing the bag in a warm-water bath. By completely surrounding the bag in a 30° C.-37° C. water bath and agitating it periodically, a single bag or "unit" of frozen plasma may be thawed usually in thirty to forty-five minutes.

This procedure presents a number of problems. First, immersing the bag in a non-sterile water bath may contaminate the bag ports, such that the thawed blood or blood components are tainted as they are withdrawn from the bag. Immersing the bag in a warm water bath can also cause any labels affixed to the bag to become detached. Even if the labels remain attached to the bag, the warm water bath often causes the labels to become wrinkled, such that it becomes impossible to scan a bar code which may be imprinted on the label. Additionally, any interruption in the integrity of the bag can permit an exchange of water and plasma, thereby contaminating both the product and the water bath. The most common form of interruption in the integrity of the bag is "edge damage" resulting from impact of the bag edges with any hard object while at low temperatures. This results in fracture of the PVC bags in 5-10% of all bags produced. Further, the water bath process cannot be accelerated, such as by exposing the blood or blood components to a higher temperature bath, since subjecting frozen plasma to any larger thermal gradient in an effort to speed up the procedure can result in physical stress and possible damage to the normal protein configuration of the plasma, and since subjecting whole blood or platelets to a higher thermal gradient can possibly damage cellular structures. The requirement of a thawing period of from thirty to forty-five minutes renders the use of frozen blood or blood components impractical for emergency trauma cases, where the patient may have an immediate need for the product and cannot afford the luxury of waiting for frozen blood or blood components to be thawed. Medical facilities cannot anticipate possible needs of blood and blood components by thawing a number of units in advance, since the requirement that each unit be typed and cross-matched to the specific patient for which it is intended would require thawing an inordinate number of units which would not be used. Furthermore, since the product cannot be safely refrozen once thawed, units which are thawed in anticipation of possible use must be discarded if the anticipated use does not arise.

Accordingly, there is a need to provide a hygienic method and apparatus for the thawing of fresh-frozen blood and blood components which does not expose the ports or the contents of the bag to the possibility of contamination.

There is a further need to provide a method and apparatus for the thawing of fresh-frozen blood and blood components which is sufficiently rapid that the product can be kept frozen until only moments before it is actually needed.

There is also a need to provide a method and apparatus for the thawing of fresh-frozen blood and blood components which affords protection against damage or rupture resulting from impact of the bag edges with a hard object while at low temperatures.

A number of efforts have been made to adapt microwave ovens for thawing frozen blood components which are contained in a bag. Some of these efforts have involved attempts to adapt a conventional cavity-type microwave oven, of the type widely used for cooking foods, for use in thawing such blood components. However, conventional prior art microwave blood-thawing devices tend to thaw the blood unevenly, which can result in overheating localized portions of the blood while other portions of the blood remain frozen.

The apparatus disclosed in my prior U.S. Pat. No. 4,874,915 overcomes many of the shortcomings associated with previous devices for thawing blood and blood components with microwave illumination. The bag of frozen blood or blood components is placed within a membrane surrounded by a liquid dielectric material which is impedance-matched with the frozen product. The membrane and liquid dielectric material readily conform to the surface of the blood bag to eliminate impedance mismatches at the various interfaces. In the disclosed embodiment, a substantially uniform magnetic field is created by employing a waveguide which supports only odd-numbered harmonic wavelengths and by utilizing an RF lens to disperse the waves across the width of the blood bag. Thus, nonuniform heating resulting from standing waves caused by reflections or from uneven illumination is substantially eliminated, thereby providing uniform heating of the frozen product.

However, the apparatus and method disclosed in my aforementioned U.S. Pat. No. 4,874,915 suffers certain disadvantages common to microwave thawing devices, namely high cost, mechanical complexity, and limited portability. In certain instances, small medical facilities which may have a need for a readily available supply of blood or blood components may not be able to afford the considerable cost of a microwave blood warming device. Further, the mechanical complexity necessitates maintenance costs and may possibly cause the unit to break down at an inopportune time. Finally, microwave thawing devices do not lend themselves to ready portability.

Thus, there is a need to provide a method and apparatus for the rapid thawing of blood and blood components which can be made available to medical facilities at a relatively low cost.

There is also a need to provide a method and apparatus for the rapid thawing of blood and blood components which is mechanically simple so as to eliminate maintenance costs and substantially reduce the possibility of malfunction at an inopportune time.

There is yet another need to provide a method and apparatus for the rapid thawing of blood and blood components which is highly portable.

Conventional blood bags present further problems with the length of time required to freeze whole blood and plasma contained therein. Factor 8, the primary clotting factor in blood, deteriorates rapidly at room temperature. Absent expensive high-speed liquid immersion freezing equipment, freezing whole blood or plasma in a conventional blood bag does not occur rapidly enough to prevent deterioration of a significant proportion of the Factor 8.

Thus, there is a need to provide a method and apparatus for storing whole blood and plasma which permits freezing using conventional freezing techniques which is sufficiently rapid that deterioration of Factor 8 is reduced.

SUMMARY OF THE INVENTION

As will be seen, the present invention satisfies each of these needs unfulfilled by prior art plasma storage and thawing apparatus. Stated generally, the present invention comprises a method and apparatus for the rapid and hygienic thawing of frozen blood or blood components which does not expose the ports or the contents of the bag to the possibility of contamination. The disclosed method and apparatus are sufficiently rapid that the frozen blood or blood components can be kept frozen until only moments before they are actually needed. The disclosed method and apparatus affords protection against damage or rupture resulting from impact of the bag edges with a hard object while at low temperatures. The disclosed apparatus is mechanically simple, thereby eliminating maintenance costs and reducing the probabilities of equipment failure at inopportune moments. The apparatus does not require an extensive capital investment and can thus be made readily available to even the smallest of medical facilities. Finally, the apparatus is highly portable.

Stated somewhat more specifically, the present invention comprises a bag for the collection, freezing, storage, and rapid thawing of fluids. Front and back sheets of fluid impervious material are bonded to one another along edge portions thereof to form a bag defining a reservoir. The front and back sheets are further bonded together at a plurality of locations intermediate the edge portions to constrain the distance by which the front and back sheets can separate. The intermediate fastening locations are disposed to permit uniform filling of the reservoir. Ports are provided for introducing and discharging fluid into and out of the reservoir. When a fluid is introduced into the reservoir, the front and back sheets are constrained from separating in response to a pressure exerted by the fluid by the intermediate fastenings between the front and back sheets to constrain the width of the bag. The resulting bag permits rapid freezing and thawing of blood and blood components.

Thus, it is an object of the present invention to provide an improved storage bag for the collection, rapid freezing, and subsequent rapid thawing of blood and blood components.

It is a further object of the present invention to provide a hygienic method and apparatus for the thawing of fresh-frozen blood and blood components which does not expose the ports or the contents of the bag to the possibility of contamination.

Another object of the present invention is to provide a method and apparatus for the thawing of fresh-frozen blood and blood components which is sufficiently rapid that the product can be kept frozen until only moments before it is actually needed.

Still another object of the present invention is to provide a method and apparatus for the thawing of fresh-frozen blood and blood components which affords protection against damage or rupture resulting from impact of the bag edges with a hard object while at low temperatures.

Yet another object of the present invention is to provide a method and apparatus for the rapid thawing of blood and blood components which can be made available to medical facilities at a relatively low cost.

It is still another object of the present invention to provide a method and apparatus for the rapid thawing of blood and blood components which is mechanically simple so as to eliminate maintenance costs and substantially reduce the possibility of malfunction at an inopportune time.

It is another object of the present invention to provide a method and apparatus for the rapid thawing of blood and blood components which is highly portable.

Still another object of the present invention is to provide a method and apparatus for storing whole blood and plasma which permits freezing using conventional freezing techniques which is sufficiently rapid that deterioration of Factor 8 is reduced.

Other objects, features, and advantages of the present invention will become apparent upon reading the following specification, when taken in conjunction with the drawings and the appended claims.

DETAILED DESCRIPTION OF THE DISCLOSED EMBODIMENT

Figure 1:
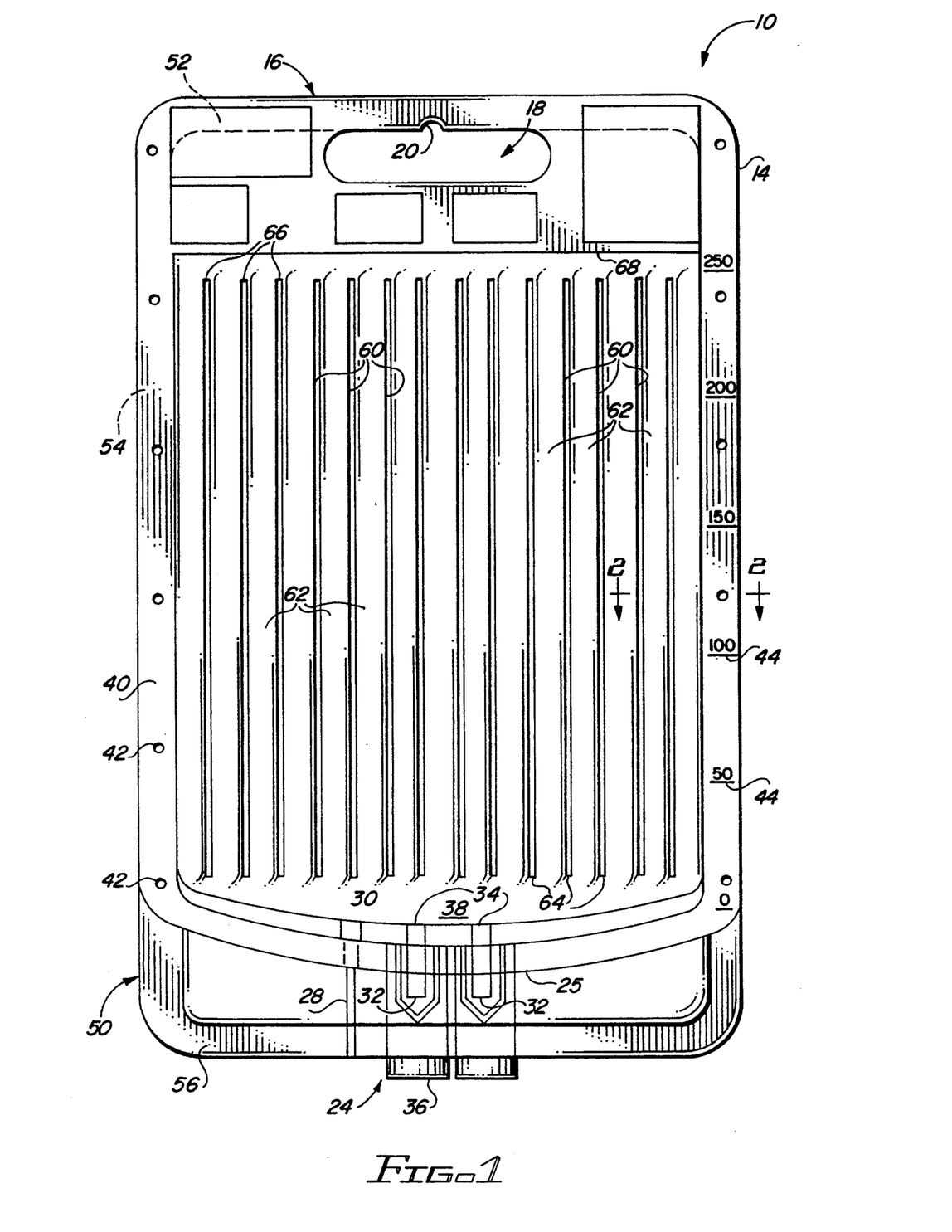
FIG. 1 is a front view of a blood bag according to the present invention.
Figure 2:
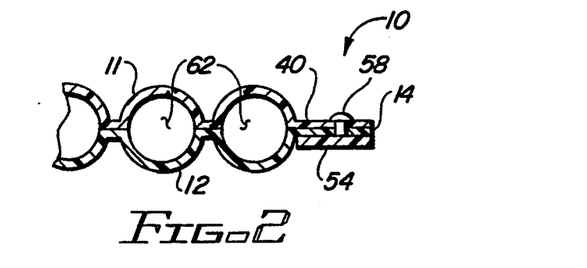
FIG. 2 is an enlarged partial transverse section view of the blood bag of FIG. 1 taken along lines 2—2 of FIG. 1.

Referring now to the drawings, in which like numerals indicate like elements throughout the several views, FIGS. 1 and 2 illustrate an improved blood bag 10 according to the present invention. The bag 10 is comprised of front and back sheets 11, 12 of 0.012 inch thick polyvinyl chloride film. The front and back sheets are ultrasonically welded, heat sealed, glued, or otherwise bonded around their marginal edges 14 to form a flexible, watertight container. The mutually facing surfaces of the front and back sheets 11, 12 are textured to eliminate interlayer cohesion which might interfere with the uniform filling of the bag. The exterior surfaces of the bag may also be textured to facilitate handling. The bag 10 further includes a top "billboard" section 16 which includes space for the standard Red Cross label set. The top section 16 includes a handle portion 18 and central hanger notch 20 for hanging the bag.

A conventional blood bag transfusion and filling port set, shown generally at 24, is located at the bottom 26 of the bag 10. The port set 24 is identical to that used on the Model 4R1423 plasma bag marketed by Fenwall Corporation. The port set 24 includes a transfer tube 28 which communicates with the interior of the bag 10 through a loading port 30. In addition, a pair of sterile transfusion tubes 32 communicate with the interior of the bag via corresponding transfusion ports 34. The transfusion tubes 32 are sealed within a seal 36 formed by opposing polymeric sheets in the manner well known to those skilled in the art to maintain the sterility of the tubes until use. The interior of the bag 10 has a generally concave bottom 38 with the ports 30, 34 disposed at the base of the concavity such that when the bag is hung in an upright position the contents of the bag are funnelled toward the ports.

Along the sides of the bag are attachment areas 40 which in the disclosed embodiment are approximately ⅜ inches wide. The front and back sheets 11, 12 are preferably sealed together across the entire width of the attachment areas 40, and a plurality of holes 42 are formed within the attachment areas at spaced-apart intervals down each side of the bag 10. A vertical scale 44 is imprinted on at least one of the bag attachment areas 40 to indicate the volume of fluid in the bag 10.

A rigid frame 50 includes a top portion 52 which spans the top of the bag 10, depending side members 54 which extend down each side of the bag, and a bottom member 56 joining the lower ends of the side members 54. The side members 54 each include a plurality of pins 58 having enlarged head portions slightly larger than the holes 42 along the sides of the bag 10 and at spaced-apart intervals to correspond to the location of the holes 42. The rigid frame 50 is removably mounted to the bag 10 by fitting each of the holes 42 along the sides of the bag onto a corresponding pin 58 on the side members 54 of the frame. When the frame 50 is mounted to the bag, the lower end of the frame extends below the bottom of the bag to protect the lower end of the bag and the transfusion and filling port set 24 from possible damage.

The front and back sheets 11, 12 of the bag 10 are ultrasonically welded or heat sealed together along a number of vertical seal lines 60 at spaced apart intervals across the width of the bag. In the disclosed embodiment, the seal lines 60 are approximately 0.625 inches on center when the bag is in its flattened, unfilled state. As can be seen in FIG. 2, when fluid is introduced into the bag, the areas between adjacent seal lines 60 are filled and expand into tubular chambers 62 which are approximately 0.375 inches in diameter. The seal lines 60 terminate at their lower ends 64 at locations spaced upwardly from the bottom 38 of the bag 10 and at their upper ends 66 at locations spaced downward from the top 68 of the bag. The spaced apart relation between the ends 64, 66 of the seal lines 60 and the respective top 68 and bottom 38 of the bag 10 places each of the tubular chambers 62 in communication with the other chambers 62 at both its upper and lower ends. This intercommunication permits the bag 10 to fill and to drain uniformly, whether the bag is in its upright or inverted orientation.

The use of the bag 10 will now be explained. The bag 10 with the rigid frame 50 mounted thereto is hung by its hanger notch 20 on a hook or the like. The bag is filled with whole blood or blood products via the transfer tube 28 and corresponding loading port 30. The textured surface of the front and back sheets 11, 12 eliminates interlayer cohesion and prevents the sheets from sticking together, thus promoting the easy and uniform filling of the bag. The volume of blood or blood components being introduced into the bag can be monitored by observing the scale 44 imprinted along the edge of the bag. As the bag fills, the chambers 62 defined within the bag by the seal lines 60 expand to a generally tubular shape, as depicted in FIG. 2. The distance by which the front and back sheets 11, 12 can separate under the outward pressure exerted by the fluid is constrained by the seal lines 60, such that the maximum thickness of the bag is controlled as the bag fills. Since the lower and upper ends 64, 66 of the seal lines 60 are spaced apart from the corresponding lower and upper ends 38, 68 of the bag 10, the bag fills uniformly across its width as fluid is introduced into the interior of the bag.

If desired, the blood bag 10 may comprise a component of a multi-bag system. Such multi-bag systems, which are commonly referred to as "tri packs" or "quad packs" depending upon the number of bags in the system, are commonly used to separate blood into its various components. In such a system, whole blood is collected in a conventional blood collection bag, and the conventional blood bag is in turn interconnected by tubes with one or more other bags, some or all of which may comprise bags 10 according to the present invention. To separate the whole blood into its respective components, the multi-bag system is placed into conventional centrifuge equipment, which exerts a force over 3000 times that of gravity. Since the rigid frame 50 cannot withstand such forces, the frame is not attached to the bag 10 until after the centrifuge procedure. The multi-bag system is centrifuged normally. Plasma is then "squeezed off" the collection bag to a communicating bag 10 through its transfer tube 28. If desired, the remaining blood components may be further separated in a similar manner. Upon completion of any separation and transfer procedures, the transfer tube 28 of the bag 10 is heat sealed to close it off at a location adjacent the lower end of the bag, and the transfer tube is then cut at a location just below the seal. Standard bloodbank labels are attached to the billboard section 16 after filling. Attachment of the frame 50 to the bag 10 is thereafter easily accomplished by engaging the pins 58 on the side members 54 of the frame from the holes 42 in the attachment areas 40 along the sides of the bag.

The sealed bag of blood or blood components is then ready for freezing.

An important feature of the bag 10 of the present invention is a means, the seal lines 60, for constraining the expansion of the filled bag 10. Because of the seal lines 60, the bag 10 in its filled configuration is only approximately 0.375 inches thick. By comparison, a filled conventional blood bag is approximately one inch thick. As a result, the frozen product in the blood bag 10 is never more than 0.188 inches from the closest exterior surface, while the frozen product in a conventional blood bag can be as much as half an inch from the closest exterior surface. Since the rate of heat transfer between the frozen product and the exterior of the bag is proportional to the distance between the two, it can be appreciated that the provision of seal lines 60 to constrain the thickness of the blood bag 10 provides greatly improved heat transfer and thus markedly lowers thaw times.

Since the bag 10 is thinner than a conventional blood bag, the height and width of the bag must be increased to provide the same capacity afforded by a conventional blood bag. The bag 10 is approximately twice as wide as a conventional blood bag. In addition, the rounded walls of the tubular chambers created by the seal lines 60 further increase the surface area over that of a conventional flat blood bag. These factors in combination provide a bag 10 having a surface area which is approximately four times greater than a conventional blood bag having the same volumetric capacity. Since the rate at which the contents of the bag gives up its heat to the exterior is proportional to the surface area of the bag, it can be appreciated that the provision of seal lines 60 to constrain the thickness of the bag 10 so as to increase the surface area of the bag further contributes to improved heat transfer and markedly lower thaw times.

The improved configuration of the bag 10 not only improves the rate at which frozen contents thaw but also reduces the time required to freeze the contents of the bag. The improved freezing time reduces the amount of time the contents of the bag are exposed to moderate temperatures and thus reduces the deterioration of Factor 8, the primary clotting factor in blood. The resulting quick-frozen blood or plasma thus includes an increased amount of Factor 8 over blood or plasma frozen in conventional collection bags.

Yet another advantage afforded by the seal lines 60 is that they provide a flexible line along which a bag 10 of frozen blood or blood components can be folded. Thus, in comparison to a conventional blood bag which is rigid when filled with solid contents, the blood bag 10 of the present invention retains a large degree of flexibility. This flexibility can improve ease of handling and facilitate the storage of the bag. Further, once the contents of the bag 10 are thawed, the bag can be folded in half and fit into a conventional pressure cuff for high-speed infusion.

A further advantage afforded by the seal lines 60 is that since the constraining means is integral with the bag structure, there is no need for any external clamping or pressing apparatus to achieve the desired configuration during freezing.

The frozen contents of the bag 10 may be thawed in a conventional manner, such as by placing the bag in a conventional warm-water bath or by exposing the bag to open air. While a conventional bag of frozen blood or blood components may require thirty minutes to thaw in a warm water bath or an hour to thaw in open air, the bag 10 of the disclosed embodiment can be thawed in a 35° C. water bath in approximately one and a half minutes and can thaw in air in approximately five minutes. Thus, the advantages of the bag 10 can be readily appreciated.

When the contents of the bag 10 have reached the desired temperature, the seals 36 at the bottom of the bag are pulled apart to expose the transfusion ports 34, and the bag is thereafter used in a conventional manner.

While the bag 10 hereinabove disclosed may be rapidly thawed in air or in a conventional warm water bath, such conventional thawing measures still suffer disadvantages. As previously mentioned, if the watertight integrity of the bag 10 has in any way been compromised during handling, the water bath will contaminate the contents of the bag. Even where the integrity of the bag 10 is maintained, the water bath risks contaminating the ports 24 of the bag. Further, a water bath suffers the disadvantage of not being easily transportable from one location to another. On the other hand, thawing a bag 10 in air, while reducing the risk of contaminating the contents of the bag or its ports, may be too slow for emergency situations. To provide a rapid thawing environment for the bag 10 which minimizes the risk for contamination of the bag or its ports, the present invention further includes a blood bag thawing unit 110.

Figure 3:
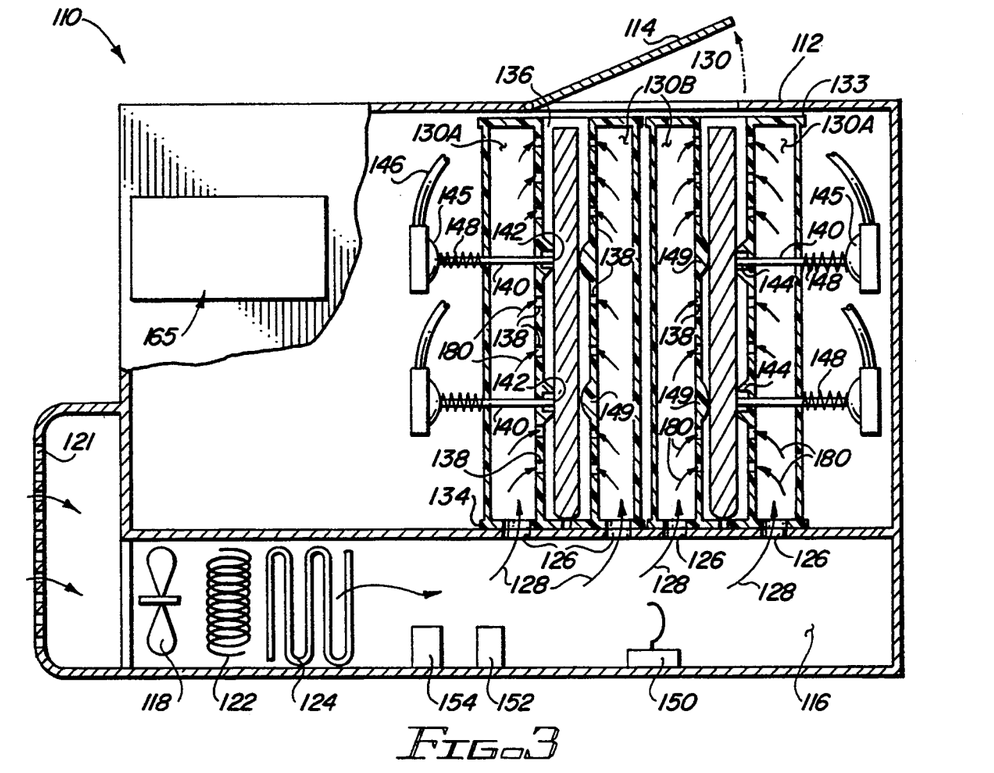
FIG. 3 is a side elevation view of an apparatus for the freezing and thawing of the blood bag of FIG. 1.
Figure 4:
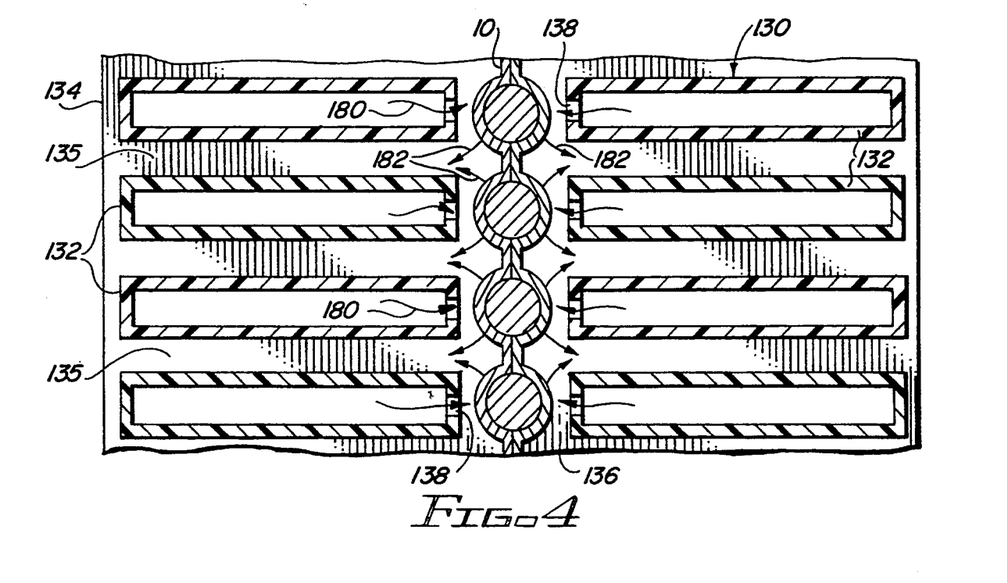
FIG. 4 is a partial top view of the duct component of the apparatus of FIG. 3.
Figure 5:
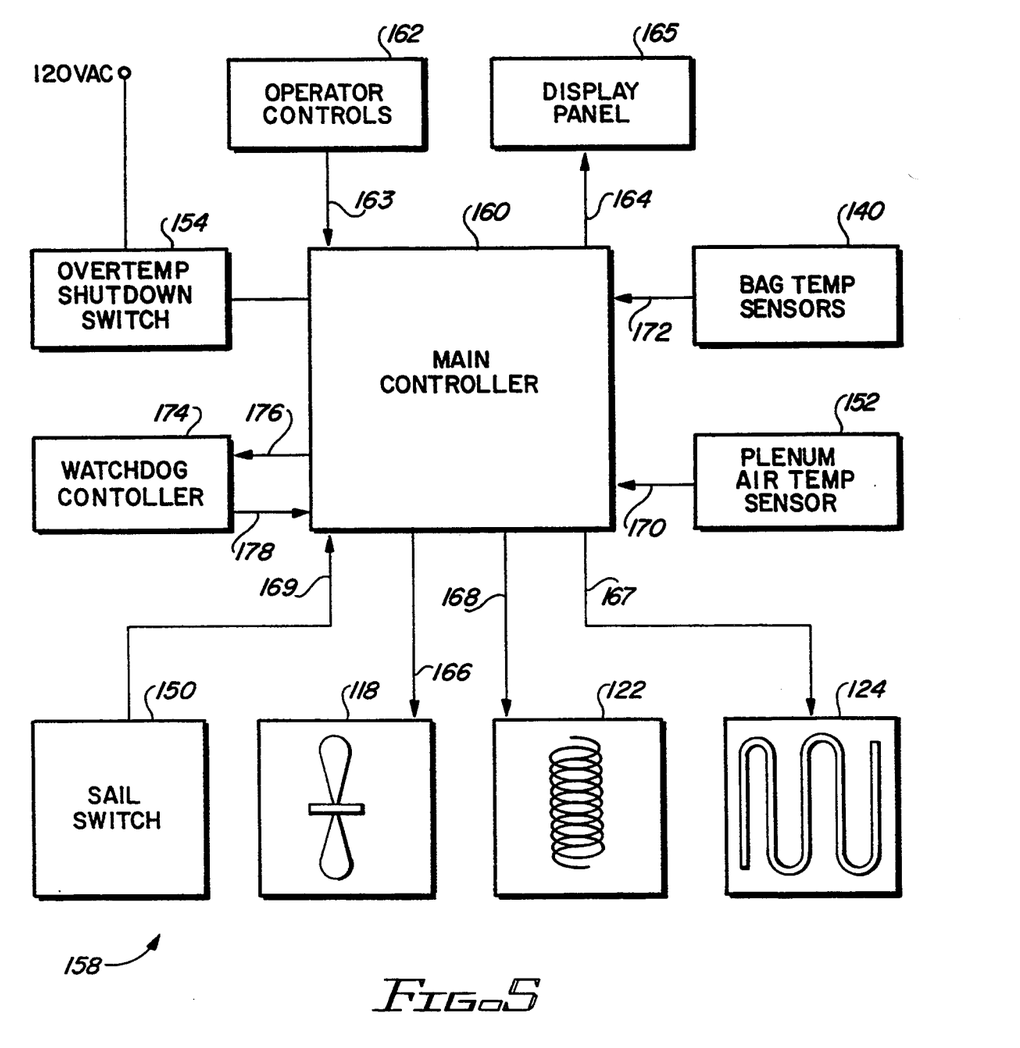
FIG. 5 is a schematic diagram of the control system of the apparatus of FIG. 3.

Referring now to FIGS. 3-5, the blood bag thawing unit 110 includes a housing 112 having a hinged lid 114 on its upper surface. In the base of the housing 112 is a plenum 116. A fan 118 driven by a conventional electric motor (not shown) is located at the left end of the plenum 116 and draws a flow of air (indicated by the arrows 120) from the housing through a vent 121 in the housing 112 and into the plenum 116. The air is blown past a conventional electrical resistive-type heating coil 122 and a conventional refrigeration-evaporator cooling coil 124 toward the right side of the plenum 116. The air flow is then directed upwardly and out through four slots 126 in the upper wall of the plenum 116, as indicated by the arrows 128.

Resting on top of the plenum 116 are two pairs of generally vertical ducts 130, each of which pairs comprises an outer duct 130A and an inner duct 130B. As can be seen in FIG. 4, each duct 130 comprises fifteen vertical tubes 132 comprised of thin-walled Plexiglass or the like. The tubes 132 are maintained in parallel, spaced-apart relation by means of upper and lower brackets 133,134, also of Plexiglass or other suitable material. In the disclosed embodiment, each tube is generally rectangular in cross section and measures 0.25 inches wide by 2.0 inches deep, and the tubes are 0.375 inches on center. Thus, each adjacent pair of tubes defines a vertical slot 135 therebetween which is approximately 0.125 inches wide. The height and width of the ducts 130 substantially corresponds to the height and width of a bag 10, and each pair of ducts 130 is spaced apart by a distance sufficient to receive a vertically oriented blood bag 10 therebetween, thus defining a vertical thawing chamber 136 between the outer and inner ducts 130A, 130B.

The ducts 130 rest on top of the plenum 116 and are aligned with the slots 126 in the upper wall of the plenum so that the air exiting through the slots 126 is directed upwardly through the tubes 132. The lower bracket 134 blocks the lower end of the vertical slots 135 between adjacent tubes 132, thereby ensuring that the air exiting through the slots 126 will flow upwardly through the tubes rather than between them.

Each pair of ducts 130 has a plurality of vents 138 located on mutually facing portions thereof so as to direct a flow of air against the adjacent surface of the blood bag 10 disposed within the vertical chamber 136 between the ducts 130A, 130B. The vents 138 of the disclosed embodiment are circular holes 0.0625 inches in diameter. This dimension is selected to achieve a relationship between the size of the vents 138 and the cross-sectional area of the vertical tubes 132 which will provide a substantially equal exit airflow through each of the vents 138 irrespective the the location of the vent along its tube.

Each outer duct 130A includes upper and lower bag temperature sensors 140. The sensing tip 142 of the sensors 140 faces inwardly and is surrounded by an insulative spacer 143 which protects and thermally isolates the sensor. Above and below each insulative spacer 143 are deflectors 144 which are bevelled to deflect the edge of a blood bag 10 being inserted into or withdrawn from the apparatus 110, again to protect the sensors 140 from damage. Each sensor 140 projects through its corresponding duct 130A and extends outwardly thereof. A diaphragm 145 is operatively associated with each sensor 140 and is in communication with the interior of the ducts 130A by means of an air line 146. A coil spring 148 is disposed around each sensor 140 and biases the sensor outwardly. Air flowing through the ducts 130A inflates the diaphragm 145 and moves the corresponding sensor 140 inwardly, overcoming the force of the associated coil spring 148 and biasing the sensor tip 142 into intimate contact with the mutually facing surface of the bag 10. A stop element 149 on the mutually facing surface of the corresponding inner duct 130B prevents the bag 10 from being displaced away from the temperature sensor 140. When the airflow through the ducts 130A is discontinued, the diaphragm 145 is no longer actuated, and the coil springs 148 bias the sensors 140 outwardly, retracting the sensor tip 142 and its insulative spacer 143.

Located within the plenum 116 is a sail switch 150 for detecting airflow within the plenum. Also located within the plenum 116 is a plenum temperature sensor 152. Finally, a bimetal overtemp shutdown switch 154 is located within the plenum and is operatively associated with the electrical system of the apparatus 110 in the manner to be hereinbelow described.

FIG. 5 schematically depicts the control system 158 of the apparatus 110. A microprocessor-based main controller 160 receives signals from operator controls 162. These controls 162 include a start switch for starting the procedure, a two-position push/pull switch for determining whether a thawing or freezing procedure is to be performed, and an emergency stop switch. The main controller also sends signals via signal path 164 to an operator display panel 165, which includes a temperature display and an alarm for audibly alerting the operator.

The main controller 160 also controls the operation of the fan 118, the heating coil 122, and the cooling coil 124 via signal paths 166, 167, and 168 respectively. The sail switch 150 located within the plenum 116 monitors the airflow within the plenum and sends a signal to the main controller 160 via signal path 169. The main controller constantly monitors the sail switch 150 and powers the heating coil 122 or cooling coil 124 only when proper airflow is detected. The plenum temperature sensor 152 is disposed within the plenum 116 and sends a signal to the main controller 160 via a signal path 170. During a thawing procedure, the main controller 160 monitors the plenum temperature detected by the plenum temperature sensor 152 and powers the heating coil on or off as necessary to maintain the air temperature in the plenum at 35° C. Finally, the bimetallic overtemp shutdown switch 154 is wired into the electric circuit powering the thawing unit 110 and monitors the plenum temperature, interrupting the electrical power to the apparatus if the plenum temperature exceeds 40° C.

During a thawing or freezing procedure, the controller 160 continuously receives signals from each of the bag temperature sensors 140 via a signal path 172. The controller 160 constantly monitors the bag temperatures and sends a signal to the operator display panel 165 via the signal path 164 to display the bag temperatures. The main controller 160 also constantly monitors the operator controls 162 and shuts down the apparatus 110 if activation of the emergency stop button is detected. When the temperature of the bags reaches 30° C. in a thawing cycle or −30° C. in a freezing cycle, the controller shuts down the heating coil 122 or cooling coil 124 and signals the operator via the operator display 165 that the procedure is complete. At the termination of a thawing cycle, the controller 160 is programmed to continue running the fan 118 for five seconds after the heating coil 122 is deactivated to dissipate heat remaining in the coil. Similarly, at the termination of a freezing cycle, the fan 118 will continue to run for five seconds to evaporate the refrigerant remaining in the evaporator coil 124.

During both the heating and the cooling procedures, a watchdog controller 174 constantly monitors the activities of the main controller 160 via signal path 176. If the watchdog monitor 172 detects any abnormality, the watchdog monitor sends a signal via signal path 178 to shut down the apparatus 110.

Operation of the apparatus to freeze a bag 10 of frozen blood or blood products will now be described. The operator opens the door 114 in the top of the housing 112 and lowers a bag 10 of frozen blood or blood products into the thawing chamber 136 between one of the pairs of ducts 130. If only a single bag 10 is to be frozen, the bag may be placed into the thawing chamber 136 defined by either of the pairs of ducts 130. If two bags 10 are to be frozen simultaneously, one bag is lowered into each thawing chamber 136. The bevelled deflectors 144 above each bag temperature sensor 140 bias the lower edge of the bag 10 inwardly and protect the sensor tip 142 from damage. With the bags 10 thus positioned within the apparatus 110, the operator actuates the controls 162 to initiate the freezing process.

Upon receiving the signal from the operator controls 162 to initiate the freezing procedure, the main controller 160 actuates the fan 118. When the sail switch 150 detects the necessary minimum airflow within the plenum 116, the controller 160 actuates the refrigeration coil 122. The fan 118 draws air from the housing 112 and into the plenum 116 in the direction indicated by the arrows 120. The air is blown past the refrigeration coil 122, cooling the air.

The flow of refrigerated air is then forced through the slots 126 in the upper wall of the plenum 116 and into the ducts 130 to flow upwardly through the tubes 132, as indicated by the arrows 128. As the tubes 132 fill with air, the diaphragms 145 are pressurized and bias the bag temperature sensors 140 inwardly until the sensor tip 142 is brought into intimate contact with the adjacent surface of the bag 10. The stop elements 149 on the mutually facing surface of the opposite duct 130B hold the bag 10 in place and prevent the bag from being displaced away from the bag temperature sensors 140.

Meanwhile, the refrigerated air flows out the vents in the ducts 130 to impinge upon the adjacent surface of the bag 10, as indicated by the arrows 180. In the disclosed embodiment, the impinging air is travelling at a velocity of sixty to seventy miles per hour. The stream of air then flows through the vertical slots 135 between adjacent tubes 132, as indicated by the arrows 182, and away from the bag 10.

The contents of the bag 10 are rapidly cooled by the flow of refrigerated air impinging upon the surface of the bag. In the disclosed embodiment, the contents of the bag 10 are uniformly chilled to a temperature of −30° C. in approximately five minutes. When the highest temperature detected by any of the bag temperature sensors 140 is −30° C., the main controller 160 shuts off the power to the refrigeration coil 124 and signals the operator audibly and visually that the cycle is complete. The fan 118 continues to run for approximately five seconds after the cooling coil 124 is deactivated to evaporate the refrigerant remaining in the evaporator coil 124. When the fan 118 shuts off, the diaphragms 145 are no longer pressurized, and the coil springs 148 retract the sensors 140 and their respective insulative spacers 143 and away from the surface of the bag 10. The operator then opens the lid 114 in the top of the housing 112 and withdraws the bags of frozen blood from the apparatus 110. The deflectors 144 deflect the bag 10 toward the center of the chamber 136 as the bag is withdrawn from the unit, thereby protecting the sensor tip 142. The frozen blood is now transported to conventional refrigerated storage facilities.

Operation of the apparatus to thaw a bag 10 of frozen blood or blood products will now be described. The operator opens the door 114 in the top of the housing 112 and lowers a bag 10 of frozen blood or blood products into the thawing chamber 136 between one of the pairs of ducts 130 in the same manner hereinabove described with respect to the freezing process. With the bags 10 thus positioned within the apparatus 110, the operator actuates the controls 162 to initiate the thawing process.

Upon receiving the signal from the operator controls 162 to initiate a thawing procedure, the main controller 160 actuates the fan 118. When the sail switch 150 detects the necessary minimum airflow within the plenum 116, the controller 160 actuates the heating coil 122. The fan 118 draws air from the housing 112 and into the plenum 116 in the direction indicated by the arrows 120. The air is blown past the heating coil 122, heating the air. The plenum temperature sensor 152 senses the air temperature within the plenum 116 and signals the main controller 160. If the plenum air temperature is below 35° C., the main controller 160 cycles the heating element 122 on. If the plenum air temperature is above 35° C., the main controller 160 cycles the heating element 122 off. Thus, the main controller 160 is operative to regulate the heating element 122 to maintain an air temperature of approximately 35° C.

The flow of heated air is then forced through the slots 126 in the upper wall of the plenum 116 and into the ducts 130 to flow upwardly through the tubes 132, as indicated by the arrows 128. As the tubes 132 fill with air, the diaphragms 145 are pressurized and bias the bag temperature sensors 140 inwardly until the sensor tip 142 is brought into intimate contact with the adjacent surface of the bag 10. The stop elements 149 on the mutually facing surface of the opposite duct 130B hold the bag 10 in place and prevent the bag from being displaced away from the bag temperature sensors 140.

Meanwhile, the heated air flows out the vents in the ducts 130 to impinge upon the adjacent surface of the bag 10, as indicated by the arrows 180. In the disclosed embodiment, the impinging air is travelling at a velocity of sixty to seventy miles per hour. The stream of air then flows through the vertical slots 135 between adjacent tubes 132, as indicated by the arrows 182, and away from the bag 10. The constant flow of air impinging upon the surface of the bag 10 and then being carried away prevents the air at the bag interface from ever reaching the dew point, thus preventing condensation on the surface of the bag.

The frozen contents of the bag 10 are rapidly heated by the flow of heated air impinging upon the surface of the bag. As the contents of the bag 10 begin to thaw, the constant pressure exerted by the energized diaphragms 145 biases the tip 142 of the sensors 140 inwardly so as to provide a temperature reading near the core of the bag 10. In the disclosed embodiment, the contents of the bag 10 are uniformly warmed to a temperature of 30° C. in approximately four minutes. When the bag temperature sensors 140 detect a temperature of 30° C., the main controller 160 shuts off the power to the heating coil 122 and signals the operator audibly and visually that the cycle is complete. The fan 118 continues to run for approximately five seconds after the heating coil 122 is deactivated to dissipate residual heat in the heating coil and plenum 116. When the fan 118 shuts off, the diaphragms 145 are no longer pressurized, and the coil springs 148 retract the sensors 140 and their respective insulative spacers 143 and away from the surface of the bag 10. The operator then opens the lid 114 in the top of the housing 112 and withdraws the bags of frozen blood from the apparatus 110. The deflectors 144 deflect the bag 10 toward the center of the chamber 136 as the bag is withdrawn from the unit, thereby protecting the sensor tip 142. When the bag is removed from the unit 110, it is ready for immediate use. The seals 36 at the bottom of the bag are pulled apart to expose the transfusion ports 34, and the bag is thereafter used in a conventional manner.

An important feature of the bag 10 of the present invention is the provision of seal lines 60 at intermediate locations of the bag bonding the front and back sheets 11, 12 together to divide the bag into a number of communicating chambers 62. The seal lines minimize the separation of the front and back sheets in response to an outward pressure exerted by a fluid filling the bag. This feature provides the advantage that the thickness of the bag is constrained to maximize the surface-to-volume ratio of the bag. Since the time required to thaw frozen blood and blood components is proportional to the surface area of the bag, the increased surface area achieved by minimizing the bag thickness dramatically reduces the amount of time required to thaw the contents of the bag.

Another advantage provided by the provision of the seal lines 60 at intermediate locations of the bag 10 is the increase in the surface area of the bag. At those locations where the front and back surfaces 11, 12 are fastened together, separation of the front and back sheets is constrained to a fixed distance. At locations between the fastening locations, however, fluid pressure exerted by the contents of the bag distends the bag surface outwardly. Thus a plurality of curved surfaces are formed. In the disclosed embodiments, the plurality of curved surfaces are the semicircular wall surfaces of the tubular chambers 62. These curved surfaces provide an increased surface area over the substantially planar sides of a conventional blood bag. Since heat transfer between the contents of the bag and the ambient is proportional to the surface area of the bag, freezing and thawing times are enhanced.

Another aspect of the bag 10 is the provision of a removable rigid frame 50 around the perimeter of the bag. Conventional blood bags containing frozen blood or blood components are easily damaged if the edge of the bag is bumped against a hard object. Since the frozen contents of the bag do not yield when the bag is bumped, the plastic walls of the bag, which are rigid at low temperatures, are often ruptured. When the integrity of the bag is thus violated, it becomes necessary for the entire bag to be discarded. On the other hand, a rigid frame permanently mounted to the bag would create problems with respect to centrifuging the bag to separate whole blood into its constituent components. The removable frame 50 of the disclosed embodiment thus provides protection to the bag 10 during routine handling but can be removed when necessary, such as when centrifuging the contents of the bag.

Another advantage of the rigid frame 50 is that it constrains the bag 10 in an essentially planar configuration. Thus, the flat bags can be easily stacked in a minimum of space.

While the present invention has been disclosed with respect to a bag 10 whose front and back surfaces 11, 12 are constrained along a plurality of vertical lines, it will be appreciated that similar results may be achieved by tacking the front and back surfaces together at a plurality of intermediate locations in a configuration other than vertical lines, for example, at a plurality of points rather than lines, or along angled, curved, or horizontal lines. Further, while the disclosed embodiment fastens the front and back surfaces together at intermediate locations by means of ultrasonic welding, it will be understood that alternate means of fastening the front and back sheets together may be employed, for example, heat sealing, glueing, or mechanical fasteners such as rivets or the like. Also, while the seal lines 60 of the disclosed embodiment divide the interior of the bag into distinct chambers 62 which communicate only at their upper and lower ends, it will be understood that similar results may be achieved by constraining the separation of the front and back sheets at intermediate locations in a manner which does not divide the interior of the bag into distinct chambers.

Finally, while the thickness of the bag 10 of the disclosed embodiment is constrained by actually bonding the front and back panels 11, 12 together, it will be appreciated that the thickness constraint contemplated by the present invention does not require actual bonding of the front and back panels together. Rather, the front and back surfaces may be fastened in such a way that permits some, but not unrestrained, separation of the front and back panels in response to outward pressure exerted by a fluid filling the bag.

The present invention has been disclosed with respect to a bag 10 which provides increased surface area by forming the bag into a plurality of parallel, vertical tubular structures. Since the curved surface of the tubular structures provides a greater surface area than a flat bag surface, the heat transfer rate is enhanced. However, it will be appreciated that other manners of increasing the surface area of the bag may be employed. For example, rather than a plurality of tubular structures, the front and back surfaces of the bag can be tacked together at a plurality of points to create a series of rectangular cells which communicate with vertically and horizontally adjacent cells. This "quilted" pattern provides cells which are curved both along their sides and along their tops and bottoms, thereby increasing the surface area of the bag over a conventional planar bag surface.

The rigid frame 50 of the disclosed embodiment is removably attached to the bag 10 by means of a plurality of pins 58 on the front surface of the frame which engage a corresponding plurality of cooperating holes 42 along the edges of the bag. However, it will be appreciated that other means of removably attaching the frame to the bag may be used, such as cooperating hooks and loops (such as that sold under the trademark "Velcro"). For applications which do not require subjecting the bag to centrifuging, it may be desirable to attach the frame to the bag permanently, such as by heat sealing, glueing, or mechanical fasteners such as rivets or the like.

Finally, it will be understood that the preferred embodiment has been disclosed by way of example, and that other modifications may occur to those skilled in the art without departing from the scope and spirit of the appended claims.

What is claimed is:

1. A bag for the collection, freezing, storage, and rapid thawing of a fluid, comprising:
    front and back sheets of fluid impervious material bonded to one another along edge portions thereof to define a reservoir;
    said front and back sheets further being fastened together at a plurality of locations intermediate said edge portions to constrain the expansion of said bag, said fastening locations being disposed to permit uniform filling of said reservoir; and
    port means for introducing and discharging fluid into and out of said reservoir,
    whereby when a fluid is introduced into said reservoir, said front and back sheets are constrained from separating in response to a pressure exerted by said fluid by said front and back sheets being fastened together at said plurality of locations intermediate said edge portions so as to constrain the expansion of said bag when filled with said fluid, thereby to increase the surface to volume ratio of said bag.

2. The bag of claim 1, further comprising a hanger means for hanging said bag with said port means being disposed at a lower end of said bag.

3. The bag of claim 1, further comprising a rigid frame mounted to said bag to provide stability and support to said bag.

4. The bag of claim 3, wherein said rigid frame is removably mounted to said bag.

5. The bag of claim 4, wherein said edge portions of said bag define a plurality of holes therethrough, wherein frame further comprises a plurality of pins projecting therefrom, and wherein said frame is mounted to said bag by means of said pins engaging said plurality of holes in said edge portions of said bag.

6. The bag of claim 1, wherein said front and back sheets have mutually facing surfaces, and wherein said mutually facing surfaces are textured to reduce interlayer adhesion.

7. The bag of claim 1, wherein said bag further comprises textured exterior surfaces to provide a high-friction gripping surface to facilitate handling of the bag.

8. The bag of claim 1, wherein said front and back sheets are comprised of a polymeric material, and wherein said front and back sheets are fastened together at said plurality of locations intermediate said edges by ultrasonically welding said front and back sheets together.

9. The bag of claim 1, wherein said front and back sheets are comprised of a polymeric material, and wherein said front and back sheets are fastened together at said plurality of locations intermediate said edges by heat-sealing said front and back sheets together.

10. The bag of claim 1, wherein said bag further comprises a concave lower portion, and wherein said port means is disposed within said concave lower portion to facilitate discharge of a fluid from said bag by force of gravity.

11. The bag of claim 1, further comprising an essentially planar portion attached to said bag to which labelling may be affixed in a visible manner.

12. The bag of claim 1, further comprising indicia printed on said bag for indicating the volume of the contents of said bag.

13. A method for storing blood or blood components, comprising the steps of:
collecting said blood or blood components in a bag comprising front and back bag surfaces;
constraining said front and back bag surfaces by means of restraining means integral to said bag to limit the extent to which said front and back bag surfaces can separate in response to said blood or blood components being collected in said bag; and
subjecting said bag to temperatures below the freezing temperature of said collected blood or blood components so as to freeze said collected blood or blood components.

14. A method for storing blood or blood components, comprising the steps of:
collecting said blood or blood components in a bag;
shaping the exterior surface of said bag into a plurality of curved surfaces to increase the surface area of said bag; and
subjecting said bag to temperatures below the freezing temperature of said collected blood or blood components so as to freeze said collected blood or blood components.

15. The method of claim 19, wherein said step of shaping the exterior surface of said bag into a plurality of curved surfaces to increase the surface area of said bag comprises the step of shaping said bag into a plurality of tubular structures.

16. The method of claim 19, wherein said step of collecting said blood or blood components in a bag comprises the step of collecting said blood or blood components in a bag having front and rear bag surfaces, and wherein said step of shaping the exterior surface of said bag into a plurality of curved surfaces to increase the surface area of said bag comprises the step of constraining said front and rear bag surfaces at a plurality of intermediate locations such that pressure exerted by said blood or blood components collected in said bag distends portions of said front and back bag surfaces outwardly at other than said plurality of intermediate constraining locations so as to form a plurality of curved bag surfaces.

17. A method for reducing the degradation of Factor 8 during the freezing of whole blood or plasma, comprising the steps of:
collecting said whole blood or plasma in a bag comprising front and back bag surfaces;
constraining said front and back bag surfaces by means of restraining means integral to said bag to limit the extent to which said front and back bag surfaces can separate in response to said whole blood or plasma being collected in said bag; and
subjecting said bag to a temperature below the freezing point of said whole blood or plasma.

* * * * *